United States Patent
He et al.

(10) Patent No.: US 10,600,215 B2
(45) Date of Patent: *Mar. 24, 2020

(54) IMAGE RECONSTRUCTION SYSTEM AND METHOD IN MAGNETIC RESONANCE IMAGING

(71) Applicant: SHANGHAI UNITED IMAGING HEALTHCARE CO., LTD., Shanghai (CN)

(72) Inventors: Renjie He, Houston, TX (US); Yu Ding, Houston, TX (US); Qi Liu, Houston, TX (US)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 0 days.

This patent is subject to a terminal disclaimer.

(21) Appl. No.: 16/458,405

(22) Filed: Jul. 1, 2019

(65) Prior Publication Data

US 2019/0325622 A1      Oct. 24, 2019

Related U.S. Application Data

(63) Continuation of application No. 16/174,223, filed on Oct. 29, 2018, now Pat. No. 10,373,351, which is a
(Continued)

(51) Int. Cl.
  *G06K 11/00* (2006.01)
  *G06T 11/00* (2006.01)
  (Continued)

(52) U.S. Cl.
  CPC ............ *G06T 11/008* (2013.01); *A61B 5/055* (2013.01); *A61B 5/7203* (2013.01); *G01R 33/00* (2013.01);
  (Continued)

(58) Field of Classification Search
  USPC .................................................. 382/128, 274
  See application file for complete search history.

(56) References Cited

U.S. PATENT DOCUMENTS

| 6,528,998 | B1 | 3/2003 | Zhou et al. |
| 7,202,663 | B2 | 4/2007 | Huang |

(Continued)

FOREIGN PATENT DOCUMENTS

CN        104783819 A        7/2015

OTHER PUBLICATIONS

P.B. Roemer et al., The NMR Phased Array, Magnetic Resonance in Medicine, 16: 192-225, 1990.

(Continued)

*Primary Examiner* — Ishrat I Sherali
(74) *Attorney, Agent, or Firm* — Metis IP LLC

(57) ABSTRACT

A method and system for image reconstruction are provided. Multiple coil images may be obtained. A first reconstructed image based on the multiple coil images may be reconstructed based on a first reconstruction algorithm. A second reconstructed image based on the multiple coil images may be reconstructed based on a second reconstruction algorithm. Correction information about the first reconstructed image may be generated based on the first reconstructed image and the second reconstructed image. A third reconstructed image may be generated based on the first reconstructed image and the correction information about the first reconstructed image.

20 Claims, 13 Drawing Sheets

Related U.S. Application Data continuation of application No. 15/344,757, filed on Nov. 7, 2016, now Pat. No. 10,115,212.

(51) Int. Cl.
| | |
|---|---|
| *A61B 5/055* | (2006.01) |
| *G01R 33/00* | (2006.01) |
| *A61B 5/00* | (2006.01) |
| *G01R 33/561* | (2006.01) |
| *G01R 33/565* | (2006.01) |
| *G06T 7/10* | (2017.01) |
| *G06T 7/12* | (2017.01) |
| *G06K 9/62* | (2006.01) |
| *G06T 5/00* | (2006.01) |

(52) U.S. Cl.
CPC ...... *G01R 33/5611* (2013.01); *G01R 33/5659* (2013.01); *G06K 9/6298* (2013.01); *G06T 5/002* (2013.01); *G06T 7/10* (2017.01); *G06T 7/12* (2017.01); *A61B 2576/00* (2013.01); *G06T 2207/10088* (2013.01); *G06T 2207/20021* (2013.01)

(56) References Cited

U.S. PATENT DOCUMENTS

| | | | |
|---|---|---|---|
| 7,408,345 B2 | 8/2008 | Bammer et al. | |
| 7,463,712 B2 | 12/2008 | Zhu et al. | |
| 7,511,495 B2 | 3/2009 | Kholmovski et al. | |
| 7,777,487 B2 * | 8/2010 | Ying | G01R 33/5611 324/309 |
| 7,952,355 B2 | 5/2011 | Torheim et al. | |
| 8,290,565 B2 | 10/2012 | Ehman et al. | |
| 8,488,860 B2 | 7/2013 | Uchizono et al. | |
| 8,810,242 B2 * | 8/2014 | Dannels | G01R 33/5659 324/307 |
| 9,316,707 B2 | 4/2016 | Khalighi et al. | |
| 9,940,540 B2 * | 4/2018 | Koehler | G06K 9/52 |
| 10,115,212 B2 * | 10/2018 | He | A61B 5/7203 |
| 10,247,802 B2 * | 4/2019 | Wang | G01R 33/246 |
| 10,373,351 B2 * | 8/2019 | He | G06T 7/10 |
| 2002/0158632 A1 | 10/2002 | Sodickson | |
| 2008/0187203 A1 | 8/2008 | Takai | |
| 2009/0253979 A1 | 10/2009 | Ehman et al. | |
| 2012/0163692 A1 | 6/2012 | Harvey et al. | |
| 2012/0187948 A1 | 7/2012 | Yamashita et al. | |
| 2015/0061668 A1 | 3/2015 | Dannels | |
| 2016/0061924 A1 | 3/2016 | Pipe | |
| 2017/0299682 A1 | 10/2017 | Quist et al. | |

OTHER PUBLICATIONS

H Mohamed et al., New Approach for Data Acquisition and Image Reconstruction in Parallel Magnetic Resonance Imaging, 26th National Radio Science Conference, Mar. 17-19, 2009.

Jeffrey R. Fitzsimmons et al., MRI Image Reconstruction via Homomorphic Signal Processing, ICASSP, 2005.

Deniz Erdogmus et al., Image Construction Methods for Phased Array Magnetic Resonance Imaging, Journal of Magnetic Resonance Imaging, 20: 306-314, 2004.

Uroš Vovk et al., A Review of Methods far Correction of Intensity Inhomogeneity in. MRI, IEEE Transactions on Medical Imaging, 26(3): 405-421, 2007.

Shang-Hong Lai et al., A Dual Image Approach for Bias Field Correction in Magnetic Resonance Imaging, Magnetic Resonance Imaging, 21(2) : 121-125, 2003.

\* cited by examiner

IMAGE RECONSTRUCTION SYSTEM AND METHOD IN MAGNETIC RESONANCE IMAGING

CROSS-REFERENCE TO RELATED APPLICATIONS

This application is a continuation application of U.S. patent application Ser. No. 16/174,223, filed on Oct. 29, 2018, which is a continuation application of U.S. patent application Ser. No. 15/344,757, filed on Nov. 7, 2016, the contents of each of which are hereby incorporated by reference.

TECHNICAL FIELD

The present disclosure generally relates to magnetic resonance imaging (MM), and more particularly, to an image reconstruction system and method in MRI.

BACKGROUND

MRI is a widely used medical technique. However, reconstructed images in MRI may include intensity inhomogeneity, which may ultimately cause misdiagnose. Thus, it may be desirable to develop an image reconstruction method and system that may remove or reduce intensity inhomogeneity to improve the quality of reconstructed image.

SUMMARY

The present disclosure relates to MRI. One aspect of the present disclosure relates to a method for image reconstruction. The method may include one or more of the following operations. Multiple coil images may be obtained. A first reconstructed image based on the multiple coil images may be reconstructed according to a first reconstruction algorithm. A second reconstructed image based on the multiple coil images may be reconstructed according to a second reconstruction algorithm. Correction information about the first reconstructed image may be generated based on the first reconstructed image and the second reconstructed image. A third reconstructed image may be generated based on the first reconstructed image and the correction information about the first reconstructed image.

In some embodiments, the first reconstruction algorithm may be a sum of squares algorithm.

In some embodiments, the second reconstruction algorithm may be a geometric average algorithm.

In some embodiments, the reconstructing a first reconstructed image or the reconstructing the second reconstructed image may include one or more of the following operations. For each point of a plurality of points in the imaged object, pixel coordinates of corresponding pixels in the multiple coil images relating to the point of the imaged object may be determined. Pixel values of the corresponding pixels in the multiple coil images of the point may be obtained. The first reconstructed image or the second reconstructed image may be reconstructed based on the pixel coordinates and the pixel values of the corresponding pixels in the multiple coil images of the plurality of points in the imaged object.

In some embodiments, the correction information may relate to intensity inhomogeneity of the first reconstructed image.

In some embodiments, the generating correction information relating to the intensity inhomogeneity of the first reconstructed image may further include dividing the first reconstructed image by the second reconstructed image to generate a divided image.

In some embodiments, the generating a third reconstructed image may further include dividing the first reconstructed image by the divided image.

In some embodiments, the generating correction information relating to the intensity inhomogeneity further include one or more of the following operations. The divided image may be smoothed to generate a smoothed divided image. The smoothed divided image may be normalized to generate a normalized image.

In some embodiments, the generating a third reconstructed image may further include dividing the first reconstructed image by the normalized image.

A further aspect of the present disclosure relates to a system for image reconstruction. The system may include a coil image generation module, a reconstruction module and a correction module. The coil image generation module may be configured to generate multiple coil images. The reconstruction module may be configured to generate a first reconstructed image based on the multiple coil images based on a first reconstruction algorithm and generate a second reconstructed image based on the multiple coil images based on a second reconstruction algorithm. The correction module may be configured to generate a third reconstructed image by correcting the first reconstructed image based on the second reconstructed image.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. The drawings are not to scale. These embodiments are non-limiting exemplary embodiments, in which like reference numerals represent similar structures throughout the several views of the drawings, and wherein.

DETAILED DESCRIPTION

Figure 1:
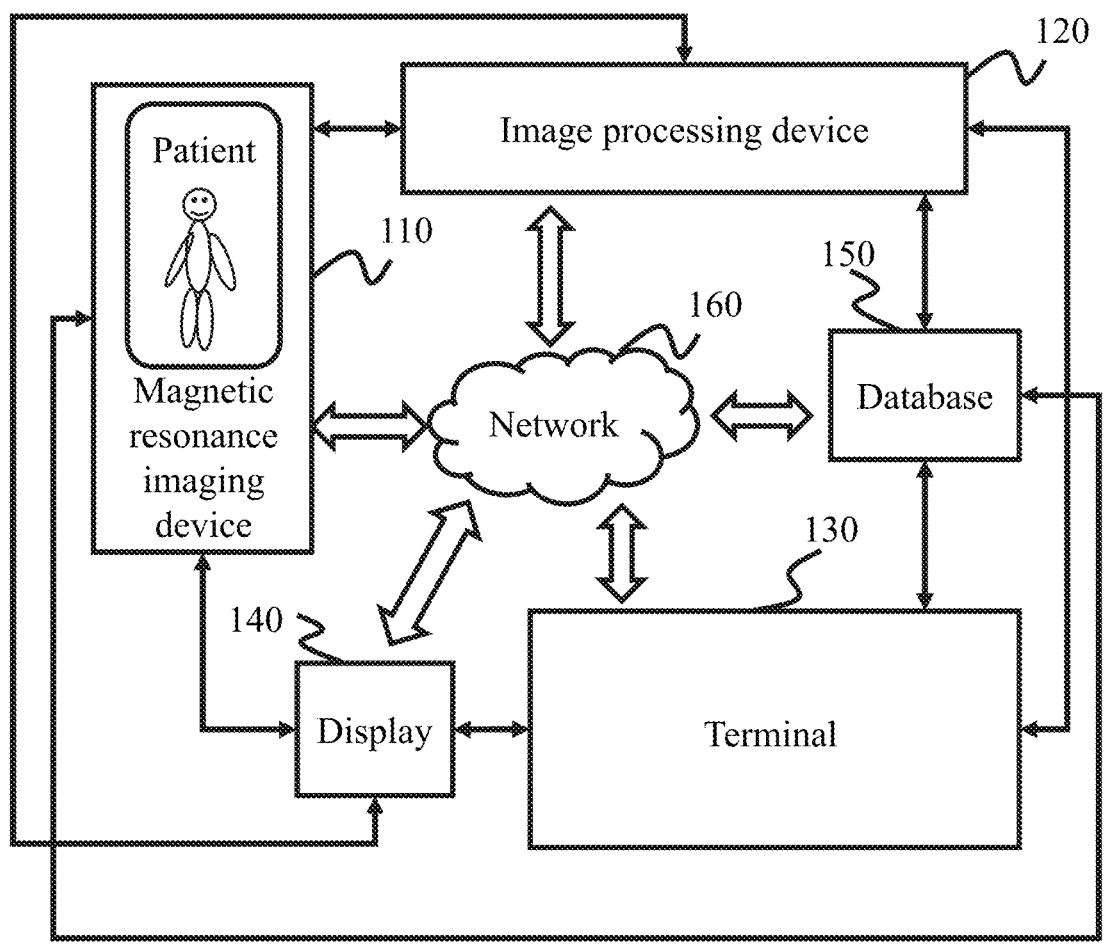
FIG. 1 illustrates a schematic diagram of an imaging system 100 according to some embodiments of the present disclosure.

In the following detailed description, numerous specific details are set forth by way of examples in order to provide a thorough understanding of the relevant disclosure. However, it should be apparent to those skilled in the art that the present disclosure may be practiced without such details. In other instances, well known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

It will be understood that the term "system," "engine," "unit," "module," and/or "block" used herein are one method to distinguish different components, elements, parts, section or assembly of different level in ascending order. However, the terms may be displaced by other expression if they may achieve the same purpose.

It will be understood that when a unit, engine, module or block is referred to as being "on," "connected to," or "coupled to" another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

The terminology used herein is for the purposes of describing particular examples and embodiments only, and is not intended to be limiting. As used herein, the singular forms "a," "an," and "the" may be intended to include the plural forms as well, unless the context clearly indicates otherwise. It will be further understood that the terms "include" and/or "comprise," when used in this disclosure, specify the presence of integers, devices, behaviors, stated features, steps, elements, operations, and/or components, but do not exclude the presence or addition of one or more other integers, devices, behaviors, features, steps, elements, operations, components, and/or groups thereof.

The present disclosure provided herein relates to relates to magnetic resonance imaging (MRI). Specially, the present disclosure relates to an image reconstruction system and method in MRI. According to some embodiments of the present disclosure, the method may include obtaining multiple coil images and generating a first reconstructed image and a second reconstructed image based on the multiple coil images using two reconstruction algorithms. The method may further including generating correction information about the first reconstructed image based on the first and the second reconstructed image and correcting the first reconstructed image based on the correction information.

FIG. 1 illustrates a schematic diagram of an imaging system 100 according to some embodiments of the present disclosure. Imaging system 100 may include a magnetic resonance imaging (MRI) device 110, an image processing device 120, a terminal 130, a display 140, a database 150, and a network 160. In some embodiments, at least part of image processing device 120 may be implemented on computer 200 shown in FIG. 2.

MRI device 110 may obtain MR image data. The MR image data may include spatial encoding information about an imaged object. The MR image data may also be referred to as K space data. The MR image data may be transferred to imaging processing device 120. Imaging processing device 120 may process the MR data to generate an MR image. In some embodiments, the MR image data may include one or more MR signals.

MRI device 110 may include an MRI scanner, a main magnet, a gradient magnet system, and a radiation frequency (RF) system (not shown in FIG. 1), or the like, or a combination thereof. The MRI scanner may be configured to place an imaged object. The MRI scanner may be a tunnel type MRI scanner 150 (i.e., a close-bore MRI scanner etc.), or an open MRI scanner (i.e., an open-bore MRI scanner etc.).

A main magnet of MRI device 110 may generate a static magnetic field during a process of imaging. The main magnet may be of various types including, a permanent magnet, a superconducting magnet, an electromagnet, or the like, or a combination thereof. The main magnet may have any magnetic field intensity, for example, 0.35 T, 0.5 T, 1 T, 1.5 T, 3 T, etc. Merely by way of example, the magnetic field intensity of the main magnet may be 1.5 T.

A gradient magnet system of MRI device 110 may generate magnet field gradients to a main magnet field in one or more directions. For example, the gradient magnet system may generate field gradients to the main magnet field in x, y, and z directions. The gradient magnet system may include a plurality of gradient coils in different directions.

An RF system of MRI device 110 may include a RF transmitter coil and a RF receiver coil. The RF transmitter coil and/or the RF receiver coil may be a birdcage coil, a transverse electromagnetic coil, a surface coil, a saddle coil, a solenoid coil, a saddle coil, a flexible coil, or the like, or a combination thereof. The RF transmitter coil may transmit RF field towards the imaged object to generate magnetic resonance phenomenon. The RF transmitter coil may transmit RF pulse with any echo time (TE) and repetition time (TR). The TE of RF pulse may be any positive number, for example, 1 millisecond, 2 milliseconds, 30 milliseconds, 100 milliseconds, or the like, or a combination thereof. Merely by way of example, the TE of RF pulse may be 2.2 milliseconds. The TR pulse may be any positive number, for example, 1 millisecond, 2 milliseconds, 30 milliseconds, 100 milliseconds, or the like, or a combination thereof. In some embodiments, the TR of RF pulse may be 4.9 ms.

An RF receiver coil of MRI device 110 may receive and/or amplify MR signal. In some embodiments, MRI device 110 may include multiple RF receiver coils. The multiple RF receiver coils may have various spatial sensitivity and may receive MR signals in parallel.

In some embodiments, MRI device 110 may include an analog-to-digital converter (ADC) (not shown in FIG. 1). The analog-to-digital converter may convert MR signals received by one or more RF receiver coils into MR image data. The analog-to-digital converter may be a direct-conversion ADC, a successive-approximation ADC, a ramp-compare ADC, a Wilkinson ADC, an integrating ADC, a delta-encoded ADC, a pipeline ADC, a sigma-delta ADC, or the like, or a combination thereof.

Image processing device 120 may generate and/or process an MR image. The MR image may be a coil image, a reconstructed MR image, a diffusion-weighted image, a diffusion tensor image, a perfusion-weighted image, a functional MR image, a sensitivity weighted image, an MR spectroscopy image, or the like, or a combination thereof. The MR image may be a four-dimensional (4D) image, a three-dimensional (3D) image, a two-dimensional (2D) image, or the like, or a combination thereof. The MR image may be an image of any object (e.g., a brain, a breast, a heart, an anocelia, an abdominal, etc.).

An MR image may have any pixel bandwidth (BW). For example, the BW of an MR image may be 20 Hz/pixel, 100 Hz/pixel, 300 Hz/pixel, or the like. Merely by way of example, the BW of an MR image may be 345 Hz/pixel. The MR image may have any field-of-view (FOV). For example, the FOV of an MR image may be 40*40 mm, 256*256 mm, 192*256 mm, or the like. In some embodiments, the FOV of an MR image may be 260*260 mm. The MR image may have any resolution. For example, the resolution of MR image may be 256*256, 1024*1024, 2048*2048, or the like. In some embodiments, the resolution of an MR image may be 256*256.

In some embodiments, an MR image may be a coil image. Image processing device 120 may generate a coil image based on MR image data. The MR image data may also be referred to as K space data. The MR image data may include spatial encoding information about an imaged object. The MR image data may be obtained by MRI device 110 or retrieved from another source (e.g., database 150, a storage, etc.). Merely by way of example, image processing device 120 may generate the coil image based on MR image data using a Fourier transform algorithm. In some embodiments, MRI device 110 may include multiple RF receiver coils. Image processing device 120 may generate multiple coil images corresponding to each RF receiver coil.

Image processing device 120 may generate a reconstructed MR image based on MR image data or multiple coil images. The MR image data may be obtained by MRI device 110 or retrieved from another source (e.g., database 150, a storage, etc.). The multiple coil images may be generated by image processing device 120 or retrieved from another source (e.g., database 150, a storage, etc.). More descriptions about the generation of a reconstructed image based on multiple coil images may be found elsewhere in the present disclosure. See, for example, FIG. 5 and the description thereof.

Imaging processing device 120 may process an MR image. Exemplary processing may include enhancing an image to generate an enhanced image, extracting some information from an image, correcting intensity inhomogeneity of an image, or the like, or a combination thereof. Image processing may include performing one or more operations on the image. Exemplary operations may include image manipulation (e.g., rotating, flipping, resizing, cropping, etc.), image correction, image weighting, image subtraction, image division, image segmentation, image binarization, image overlapping, image matching, image negative film development, image noise reduction, image enhancement, image compression, or the like, or a combination thereof. Exemplary image correction may include intensity inhomogeneity correction, image distortion correction, gradient nonlinearity correction, motion artifact correction, color correction, or the like, or a combination thereof.

Image processing device 120 may be any kind of device that may process an image. For example, image processing device 120 may include a high-performance computer specialized in image processing or transaction processing, a personal computer, a portable device, a server, a microprocessor, an integrated chip, a digital signal processor (DSP), a pad, a PDA, or the like, or a combination thereof. In some embodiments, imaging processing device 120 may be implemented on computer 200 shown in FIG. 2.

Image processing may involve an image reconstruction technique, an intensity inhomogeneity correction technique, or the like, or a combination thereof. As used herein, "correcting" intensity inhomogeneity may refer to completely or partially remove intensity inhomogeneity that is present or identified by an image processing technique.

Image reconstruction technique applicable to MR image data may include a simultaneous acquisition of spatial harmonic (SMASH) algorithm, an AUTO-SMASH algorithm, a variable density AUTO-SMASH algorithm, a generalized auto-calibrating partially parallel acquisition (GRAPPA) algorithm, a generalized-SMASH algorithm, sensitivity profiles from an array of coils for encoding and reconstruction in a parallel (SPACE RIP) algorithm, or the like, or a combination thereof. The image reconstruction technique based on multiple coil images may include a sum of squares (SOS) algorithm, a geometric average (GA) algorithm, a sensitivity encoding (SENSE) algorithm, a parallel imaging with localized sensitivities (PILS) algorithm, a modified sensitivity encoding (MSENSE) algorithm, a SPACE RIP algorithm, or the like, or a combination thereof. Merely by way of example, image processing device 120 may generate a reconstructed MR image based on multiple coil images using an SOS algorithm. As another example, image processing device 120 may generate a reconstructed MR image based on multiple coil images using a GA algorithm.

Intensity inhomogeneity correction technique may include a homomorphic filtering algorithm, a homomorphic un-sharp masking (HUM) algorithm, a surface fitting algorithm, a nonparametric non-uniform intensity normalization (N3) algorithm, an bias field corrector (BFC) algorithm, a maximum-likelihood based algorithm, a fuzzy c-means algorithm, a histogram matching algorithm, or the like, or a combination thereof.

Terminal 130 may be connected to or communicate with image processing device 120. Terminal 130 may allow one or more operators (e.g., a doctor, an imaging technician, etc.) to control the production and/or display of images on display 140. Terminal 130 may include an input device, an output device, a control panel (not shown in FIG. 1), or the like, or a combination thereof. The input device may be a keyboard, a touch screen, a mouse, a remote controller, a wearable device, or the like, or a combination thereof. An input device may include alphanumeric and other keys that may be inputted via a keyboard, a touch screen (e.g., with haptics or tactile feedback, etc.), a speech input, an eye tracking input, a brain monitoring system, or any other comparable input mechanism. The input information received through the input device may be communicated to image processing device 120 via network 160 for further processing. Another type of the input device may include a cursor control device, such as a mouse, a trackball, or cursor direction keys to communicate direction information and command selections to, for example, image processing device 120 and to control cursor movement on display 140 or another display device.

Display 140 may display information. The information may include an image before and/or after image processing, a request for input or parameter relating to image acquisition and/or processing, or the like, or a combination thereof. Display 140 may include a liquid crystal display (LCD), a light emitting diode (LED)-based display, a flat panel display or curved screen (or television), a cathode ray tube (CRT), or the like, or a combination thereof.

Database 150 may store images and/or relevant information or parameters. The images may include an MR image (e.g., coil image, reconstructed MR image, etc.), a processed MR image (e.g., segmented MR image, corrected MR image, etc.). The parameters may include the magnetic field intensity, the resolution of an MR image, the TE of RF pulses, the TR of RF pulses, and the bandwidth of an MR image, the field-of-view (FOV) of an MR image, or the like, or a combination thereof.

Network 160 may establish connection between different units in imaging system 100. Network 160 may be a single network, or a combination of various networks. Network 160 may be a wired network or a wireless network. The wired network may include using a Local Area Network (LAN), a Wide Area Network (WAN), a Bluetooth, a ZigBee, a Near Field Communication (NFC), or the like, or a combination thereof. The wireless network may be a Bluetooth, a Near Field Communication (NFC), a wireless local area network (WLAN), WiFi, a Wireless Wide Area Network (WWAN), or the like, or a combination thereof.

It should be noted that the descriptions above in relation to imaging system 100 is provided for the purposes of illustration, and not intended to limit the scope of the present disclosure. For persons having ordinary skills in the art, various variations and modifications may be conducted under the guidance of the present disclosure. However, those variations and modifications do not depart the scope of the present disclosure. For example, part or all of the image generated by imaging processing device 120 may be processed by terminal 130. In some embodiments, terminal 130 and display 140 may be combined with or part of image processing device 120 as a single device. Similar modifications should fall within the scope of the present disclosure.

Figure 2:
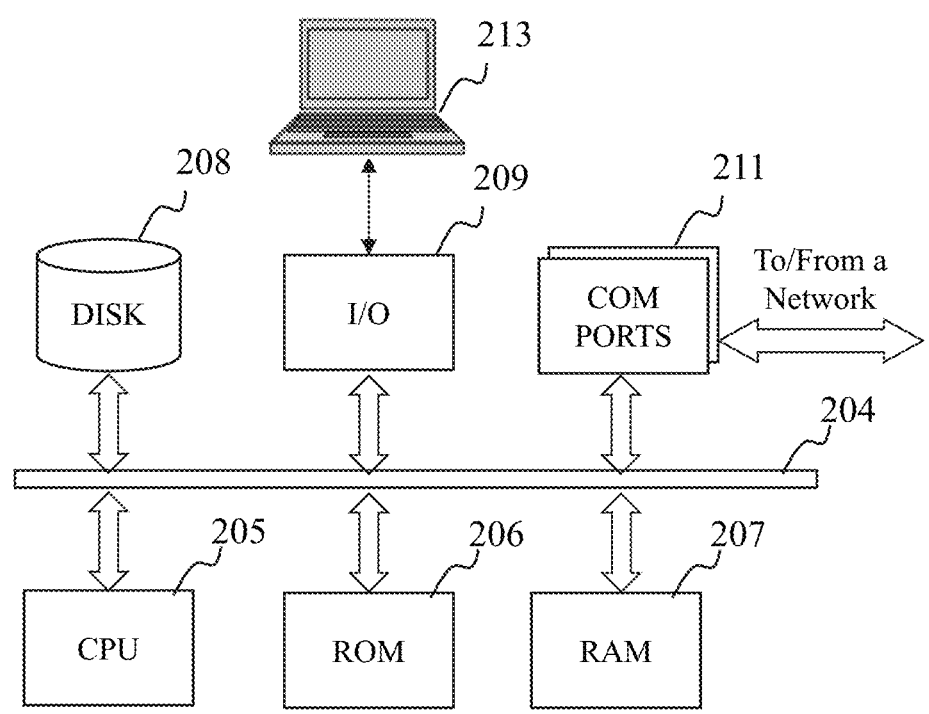
FIG. 2 illustrates an architecture of a computer on which a specialized system incorporating the present teaching may be implemented.

FIG. 2 illustrates an architecture of a computer 200 on which a specialized system incorporating the present teaching may be implemented. Such a specialized system incorporating the present teaching has a functional block diagram illustration of a hardware platform that may include user interface elements. Computer 200 may be a general purpose computer or a special purpose computer. Computer 200 may be used to implement any component of image processing as described herein. For example, image processing device 120 may be implemented on a computer such as computer 200, via its hardware, software program, firmware, or a combination thereof. Although only one such computer is shown, for convenience, the computer functions relating to image processing as described herein may be implemented in a distributed fashion on a number of similar platforms, to distribute the processing load. In some embodiments, computer 200 may be used as imaging processing device 120 shown in FIG. 1.

Computer 200, for example, may include communication (COM) ports 211 connected to and from a network connected thereto to facilitate data communications. Computer 200 may also include a central processing unit (CPU) 205, in the form of one or more processors, for executing program instructions. The exemplary computer platform may include an internal communication bus 204, program storage, and data storage of different forms, e.g., disk 208, read only memory (ROM) 206, or random access memory (RAM) 207, for various data files to be processed and/or communicated by the computer, as well as possibly program instructions to be executed by CPU 205. Computer 200 may also include an I/O component 209, supporting input/output flows between the computer and other components therein such as user interface elements 213. Computer 200 may also receive programming and data via network communications.

Aspects of the methods of the image processing and/or other processes, as described herein, may be embodied in programming. Program aspects of the technology may be thought of as "products" or "articles of manufacture" typically in the form of executable code and/or associated data that is carried on or embodied in a type of machine readable medium. Tangible non-transitory "storage" type media include any or all of the memory or other storage for the computers, processors, or the like, or associated modules thereof, such as various semiconductor memories, tape drives, disk drives and the like, which may provide storage at any time for the software programming.

All or portions of the software may at times be communicated through a network such as the Internet or various other telecommunication networks. Such communications, for example, may enable loading of the software from one computer or processor into another, for example, from a management server or host computer of a scheduling system into the hardware platform(s) of a computing environment or other system implementing a computing environment or similar functionalities in connection with image processing. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to tangible "storage" media, terms such as computer or machine "readable medium" refer to any medium that participates in providing instructions to a processor for execution.

A machine-readable medium may take many forms, including but not limited to, a tangible storage medium, a carrier wave medium or physical transmission medium. Non-volatile storage media include, for example, optical or magnetic disks, such as any of the storage devices in any computer(s), or the like, which may be used to implement the system or any of its components shown in the drawings. Volatile storage media may include dynamic memory, such as a main memory of such a computer platform. Tangible transmission media may include coaxial cables; copper wire and fiber optics, including the wires that form a bus within a computer system. Carrier-wave transmission media may take the form of electric or electromagnetic signals, or acoustic or light waves such as those generated during radio frequency (RF) and infrared (IR) data communications. Common forms of computer-readable media may include, for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a physical processor for execution.

Those skilled in the art will recognize that the present teachings are amenable to a variety of modifications and/or enhancements. For example, although the implementation of various components described herein may be embodied in a hardware device, it may also be implemented as a software only solution—e.g., an installation on an existing server. In addition, image processing as disclosed herein may be implemented as a firmware, firmware/software combination, firmware/hardware combination, or a hardware/firmware/software combination.

Figure 3A:
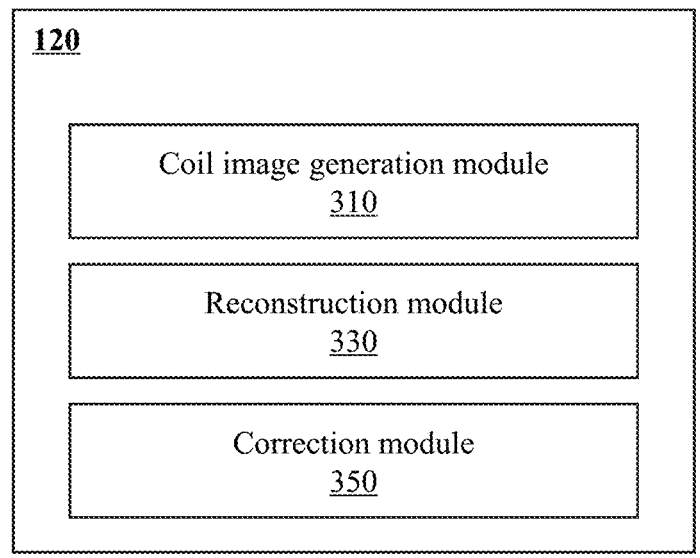
FIG. 3A illustrates an exemplary image processing device according to some embodiments of the present disclosure.

FIG. 3A illustrates an exemplary image processing device 120 according to some embodiments of the present disclosure. Image processing device 120 may include a coil image generation module 310, a reconstruction module 330, and a correction module 350. Components in image processing device 120 may be connected to or communicate with each other and/or other components in imaging system 100, for example, MRI device 110, terminal 130, display 140, database 150, or the like, or a combination thereof.

Coil image generation module 310 may generate a coil image. As used herein, a coil image may be a reconstructed MR image generated based on MR image data collected by a coil. The MR image data may be obtained by MRI device 110 or retrieved from another source (e.g., database 150, a storage, etc.). The coil image may be sent to one or more other components in image processing device 120, for example, reconstruction module 330, correction module 350, or the like, or a combination thereof. The coil image may be sent to one or more components in imaging system 100, for example, terminal 130, display 140, database 150, or the like, or a combination thereof.

In some embodiments, the MR image data may be obtained by MRI device 110. Considering that different parts of an RF receiver coil may have different sensitivity with respect to MR signals, the coil image generated based on MR image data collected by MRI device 110 may have intensity inhomogeneity.

In some embodiments, image processing device 120 may generate multiple coil images based on MR image data obtained by MRI device 110 with multiple RF receiver coils. In that case, image processing device 120 may generate a coil image corresponding to each RF receiver coil. The multiple coil images may have different intensity inhomogeneity due to the differences in the sensitivity of various RF receiver coils in MRI device 110.

Reconstruction module 330 may perform image reconstruction to generate a reconstructed image. The reconstructed image may be a 4D reconstructed MR image, a 3D reconstructed MR image, or a 2D reconstructed MR image. The reconstructed image may be a grayscale image, an RGB image, or a binary image. The reconstructed image generated by reconstruction module 330 may be sent to other component(s) in image processing device 120, for example, correction module 350, or the like, or a combination thereof. The reconstructed image may be sent to one or more components in imaging system 100, for example, terminal 130, display 140, database 150, or the like, or a combination thereof.

Reconstruction module 330 may generate a reconstructed image based on MR image data or multiple coil images. The MR image data may be obtained by MRI device 110 or retrieved from another source (e.g., database 150, a storage, etc.). The multiple coil images may be generated by coil image generation module 310 or retrieved from another source (e.g., database 150, a storage, etc.).

Reconstruction module 330 may generate multiple reconstructed images based on multiple coil images. The multiple reconstructed images may be generated based on a same coil image set or different coil image sets. As used herein, a coil image set may include one or more coil images. The multiple reconstructed images may be generated using a same algorithm or different algorithms. A first reconstructed image may be generated based on a first set of multiple coil images. A second reconstructed image may be generated based on a second set of multiple coil images. The first set of multiple coil images and the second set of multiple coil images may be the same or different. For example, the first set of multiple coil images and the second set of multiple coil images may be generated based on MR image data obtained by the same MRI device 110 at the same time or at different times. As another example, the first set of multiple coil images and the second set of multiple coil images may be generated based on MR image data obtained by different MRI devices 110 at the same time or at different times.

Reconstruction module 330 may perform image reconstruction based on an image reconstruction technique. The image reconstruction technique based on MR image data may include a SMASH algorithm, an AUTO-SMASH algorithm, a variable density AUTO-SMASH algorithm, a GRAPPA algorithm, a generalized-SMASH algorithm, a SPACE RIP algorithm, or the like, or a combination thereof. The image reconstruction technique based on multiple coil images may include an SOS algorithm, a GA algorithm, a SENSE algorithm, a PILS algorithm, an MSENSE algorithm, and a SPACE RIP algorithm, or the like, or a combination thereof.

In some embodiments, image processing device 120 may generate two reconstructed MR images based on multiple coil images. For example, a first reconstructed MR image may be reconstructed using an SOS algorithm based on a first set of coil images and a second reconstructed MR image may be reconstructed using a GA algorithm based on a second set of coil images. The first set of coil images and the second set of coil image may be the same or different.

In some embodiments, reconstruction module 330 may include a sum squares reconstruction unit 331 (shown in FIG. 3B), a geometric average reconstruction unit 333 (shown in FIG. 3B), and a storage unit (not shown in FIG. 3A). Sum of squares reconstruction unit 331 may generate a reconstructed image based on multiple coil images using an SOS algorithm. Geometric average reconstruction unit 333 may generate a reconstructed image based on multiple coil images using a GA algorithm. The storage unit may be used to storage MR image data, a reconstructed MR image, or the like, or a combine thereof.

Correction module 350 may correct an image. The image may be a coil image, a reconstructed image, or the like, or a combination thereof. The image may be generated by coil image generation module 310, reconstruction module 330 or retrieved from another source (e.g., database 150, and a storage, etc.). Correction module 350 may correct intensity inhomogeneity, distortion, gradient nonlinearity, motion artifact, or the like, or a combination thereof.

In some embodiments, correction module 350 may correct intensity inhomogeneity of an image. Intensity inhomogeneity may also be referred to as intensity nonuniformity. The brightness of an image with intensity inhomogeneity may be distributed nonuniformly. Correction module 350 may correct intensity inhomogeneity of an image based on an intensity inhomogeneity correction algorithm. The intensity inhomogeneity correction algorithm may include a homomorphic filtering algorithm, an HUM algorithm, a surface fitting algorithm, an N3 algorithm, a BFC algorithm, a maximum-likelihood based algorithm, a fuzzy c-means algorithm, a histogram matching algorithm, or the like, or a combination thereof.

In some embodiments, correction module 350 may correct intensity inhomogeneity based on two reconstructed images. The two reconstructed image may be reconstructed based on a same MR data set or a same set of multiple coil images. More descriptions about correcting intensity inhomogeneity based on two reconstructed images may be found elsewhere in the present disclosure. See., for example, FIG. 7 and FIG. 9 and the descriptions thereof.

Figure 3B:
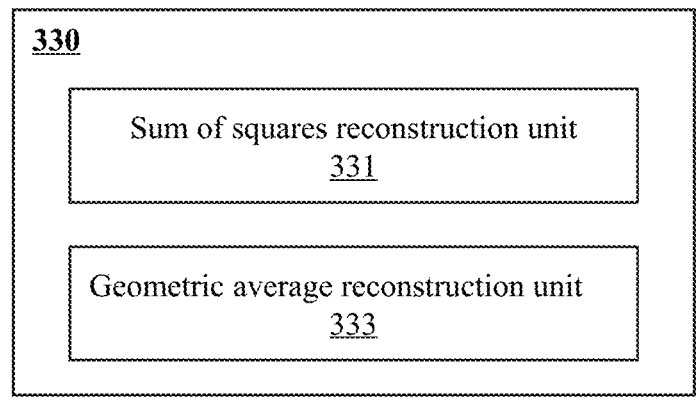
FIG. 3B illustrates an exemplary reconstruction module according to some embodiments of the present disclosure.
Figure 3C:
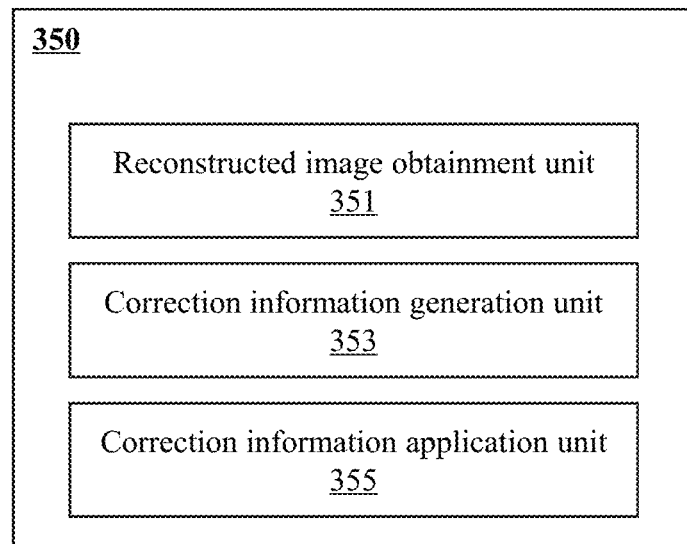
FIG. 3C illustrates an exemplary correction module according to some embodiments of the present disclosure.

In some embodiments, correction module 350 may include a reconstructed image obtainment unit 351 (shown in FIG. 3C), a correction information generation unit 353 (shown in FIG. 3C), a correction information application unit 355 (shown in FIG. 3C), and a storage unit (not shown in FIG. 3C). Reconstructed image obtainment unit 351 may obtain a reconstructed image. Correction information generation unit 353 may generate correction information of a reconstructed image. Correction information application unit 355 may correct a reconstructed image based on correction information. The storage unit may be used to storage MR image data, reconstructed MR image, correction information, or the like, or a combine thereof.

FIG. 3B illustrates an exemplary reconstruction module 330 according to some embodiments of the present disclosure. Reconstruction module 330 may include a sum of squares reconstruction unit 331 and a geometric average reconstruction unit 333.

Sum of squares reconstruction unit 331 may generate a reconstructed image based on multiple coil images using an SOS algorithm. Geometric average reconstruction unit 333 may generate a reconstructed image based on multiple coil images using a GA algorithm. More descriptions about the SOS algorithm and the GA algorithm may be found elsewhere in the present disclosure. See, for example, FIG. 5 and FIG. 9 and the descriptions thereof.

FIG. 3C illustrates an exemplary correction module 350 according to some embodiments of the present disclosure. Correction module 350 may include a reconstructed image obtainment unit 351, a correction information generation unit 353, and a correction information application unit 355.

Reconstructed image obtainment unit 351 may obtain a reconstructed image. The reconstructed image may be a 4D reconstructed image, a 3D reconstructed image, or a 2D reconstructed image. The reconstructed image may be obtained from reconstruction module 330 or retrieved from another source (e.g., a database 150, a storage, etc.). In some embodiments, reconstructed image obtainment unit 351 may obtain multiple reconstructed images. The multiple reconstructed images may be generated based on the same MR data set or different MR data sets. The multiple reconstructed images may be generated based on a same set of multiple coil images or different sets of multiple coil images. The multiple reconstructed images may be generated using a same reconstruction technique or different reconstruction techniques.

Correction information generation unit 353 may generate correction information of a reconstructed image. The correction information may include correction information related to intensity inhomogeneity, distortion information, gradient nonlinearity information, motion artifact information, or the like, or a combination thereof. The correction information may be generated by various ways.

For example, the correction information may be generated by smoothing the reconstructed image to capture or emphasize information of interest contained in the reconstructed image. As another example, the correction information may be generated by comparing the reconstructed image with another reconstructed image. The two reconstruction images may be generated based on the same MR image data or a same set of coil images. As a further example, the correction information may be generated based on spatial sensitivity of the multiple RF receiver coils. More descriptions about the correction information generation may be found elsewhere in the present disclosure. See, for example, FIG. 6 and the description thereof. In some embodiments, the correction information may be correction information related to intensity inhomogeneity. The correction information related to intensity inhomogeneity may be used to correct intensity inhomogeneity.

Correction information application unit 355 may correct a reconstructed image based on correction information. The correction information may be generated by correction information generation unit or retrieved from another source (e.g., database 150, a storage, etc.). More descriptions about the correcting reconstructed image based on correction information may be found elsewhere in the present disclosure. See, for example, FIG. 6 and the description thereof.

It should be noted that the descriptions above in relation to image processing device 120 is provided for the purposes of illustration, and not intended to limit the scope of the present disclosure. For persons having ordinary skills in the art, various variations and modifications may be conducted under the guidance of the present disclosure. However, those variations and modifications do not depart the scope of the present disclosure. For example, reconstruction module 330 may include one or more other reconstruction unit (not shown in figures) utilizing other reconstruction technique (e.g., a SENSE algorithm, a GA algorithm, a PILS algorithm, an MSENSE algorithm, SPACE RIP, etc.). As another example, correction information generation unit 350 may include a divided image generation subunit, an image smoothing subunit, and/or an image normalization subunit (not shown in figures.).

Figure 4:
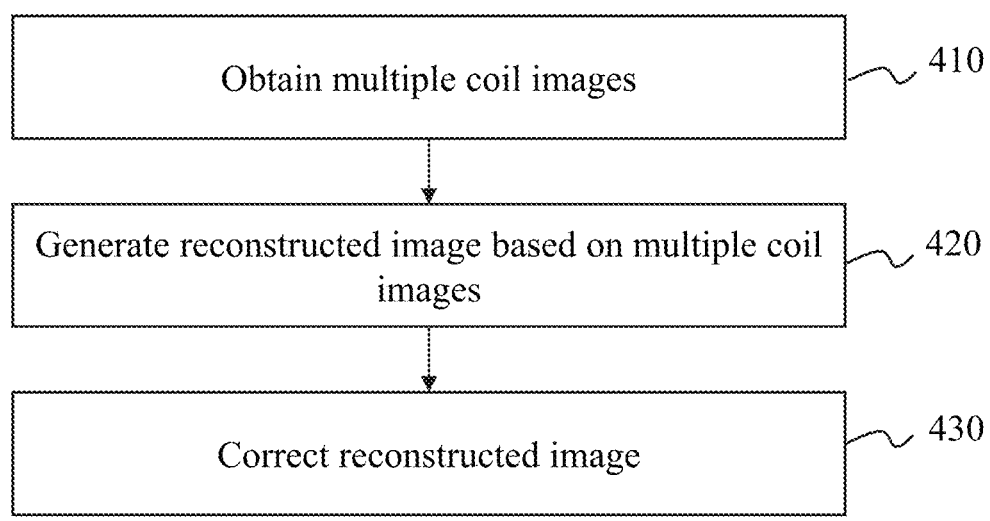
FIG. 4 illustrates a flowchart illustrating an exemplary process for image reconstruction in accordance with some embodiments of the present disclosure.

FIG. 4 illustrates a flowchart illustrating an exemplary process 400 for image reconstruction in accordance with some embodiments of the present disclosure. In some embodiments, process 400 may be performed by one or more devices (e.g., image processing device 120) in imaging system 100 (shown in FIG. 1) and image processing device 120 (shown in FIG. 3A). In some embodiments, at least part of process 400 may be performed by computer 200 shown in FIG. 2.

In 410, multiple coil images may be obtained. The multiple coil images may be generated by coil image generation module 310 or retrieved from another source (e.g., database 150, a storage, etc.). Detailed descriptions about coil images may be found elsewhere in the present disclosure. See, for example, FIG. 1 and FIG. 3 and the description thereof. In some embodiments, the multiple coil images may be generated by coil image generation module 310 based on MR image data collected by MRI device 110 of imaging system 100.

In 420, a reconstructed image may be generated based on multiple coil images. Image reconstruction in 420 may be performed by reconstruction module 330 illustrated in FIG. 3A. The reconstructed image may be generated based on multiple coil images utilizing an image reconstruction technique including an SOS algorithm, a GA algorithm, a SENSE algorithm, a PILS algorithm, and an MSENSE algorithm, a SPACE RIP algorithm, or the like, or a combination thereof. More than one reconstructed images may be generated in 420. The more than one reconstructed images may be generated based on a same coil image set or different coil image sets. The more than one reconstructed images may be generated using a same algorithm or different algorithms. Merely by way of example, the reconstructed image may be generated based on multiple coil images utilizing an SOS algorithm and/or a GA algorithm. More descriptions about the SOS algorithm and the GA algorithm may be found elsewhere in the present disclosure. See, for example, FIG. 5 and FIG. 9 and the descriptions thereof.

In 430, a reconstructed image may be corrected to generate a corrected image. The image correction in 430 may be performed by correction module 350 illustrated in FIG. 3A. The correction operation in 430 may include intensity inhomogeneity correction, distortion correction, gradient nonlinearity correction, motion artifact correction, or the like, or a combination thereof.

In some embodiments, the intensity inhomogeneity of a reconstructed image may be corrected using an intensity inhomogeneity correction algorithm. The intensity inhomogeneity correction algorithm may include a homomorphic filtering algorithm, an HUM algorithm, a surface fitting algorithm, an N3 algorithm, a BFC algorithm, a maximum-likelihood based algorithm, a fuzzy c-means algorithm, a histogram matching algorithm, or the like, or a combination thereof.

In some embodiments, correction module 350 may correct intensity inhomogeneity based on two reconstructed images. The two reconstructed images may be obtained based on a same MR data set or a same set of multiple coil images. More descriptions about correcting intensity inhomogeneity based on two reconstructed images may be found elsewhere in the present disclosure. See, for example, FIG. 7 and FIG. 9 and the descriptions thereof.

It should be noted that process 400 described above is provided for the purposes of illustration, and not intended to limit the scope of the present disclosure. Apparently for persons having ordinary skills in the art, numerous variations and modifications may be conducted under the teaching of the present disclosure. However, those variations and modifications do not depart the protection scope of the present disclosure. In some embodiments, some steps may be reduced or added. For example, 430 may be changed and a noise reduction algorithm may be used to process the reconstructed image. As another example, 420 may be omitted and intensity inhomogeneity of coil images may be corrected in 430.

Figure 5:
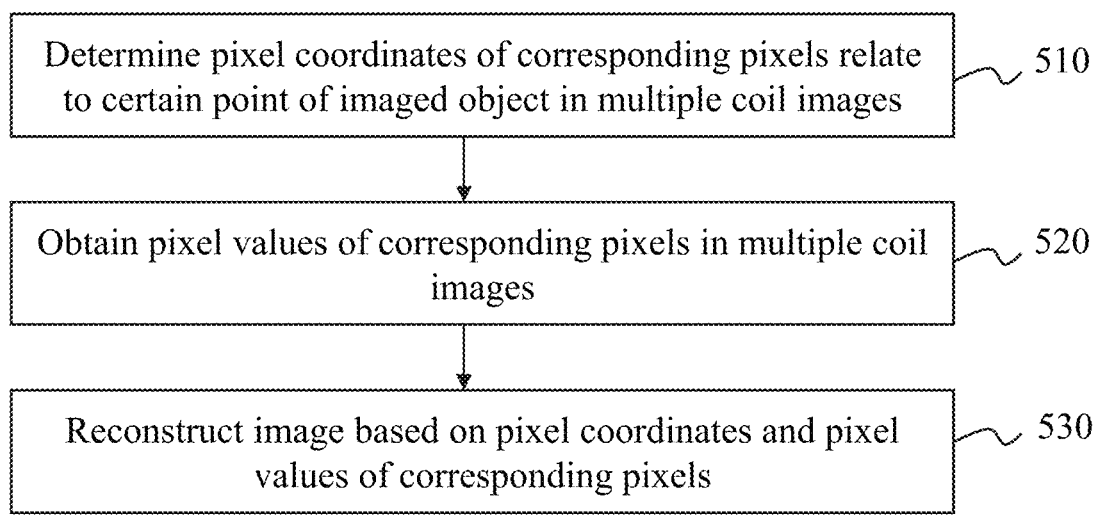
FIG. 5 is a flowchart illustrating an exemplary process for image reconstruction in accordance with some embodiments of the present disclosure.

FIG. 5 is a flowchart illustrating an exemplary process 500 for image reconstruction in accordance with some embodiments of the present disclosure. In some embodiments, process 500 may be performed by reconstruction module 330 in imaging processing device 120. In some embodiments, process 500 described with reference to FIG. 5 may be an exemplary process for achieving 420 shown in FIG. 4.

In 510, pixel coordinates of corresponding pixels in multiple coil images may be determined. The corresponding pixels in the multiple coil images may relate to a point of the imaged object. The multiple coil images may be reconstructed images of a same imaged object.

In 520, pixel values of corresponding pixels in the multiple coil images may be obtained. As used herein, a pixel value may refer to the grey value of a pixel. Suppose that there are n coil images, as for corresponding pixels of a point of the imaged object, the pixel values of the corresponding pixels may be denoted as $P_1, P_2, P_3, \ldots, P_n$.

In 530, a reconstructed image may be generated based on pixel coordinates and pixel values of corresponding pixels in the multiple coil images. The pixel value of a point in the imaged object in reconstructed image may be denoted as P. The pixel value P may be determined based on the pixel values of corresponding pixels $P_1, P_2, P_3, \ldots, P_n$. For example, the pixel value P may be a statistical parameter (e.g., an average value, a median value, a mode, a sum of squares, a geometric mean, etc.) of the pixel values of corresponding pixels $P_1, P_2, P_3, \ldots, P_n$.

In some embodiments, pixel value P may be determined based on the pixel values of corresponding pixels using an SOS algorithm. In that case, process 500 may be performed by sum of squares reconstruction unit 331 in imaging processing device 120. The SOS algorithm may be performed according to Equation (1) below:

$$P = \sqrt[2]{\sum_{i=1}^{n} P_i^2}, \tag{1}$$

where n refers to a number of the coil images.

In some embodiments, pixel value P may be determined based on the pixel values of corresponding pixels using a GA algorithm. In that case, process 500 may be performed by geometric average reconstruction unit 333 in imaging processing device 120. The GA algorithm may be performed according to Equation (2) below:

$$P = \sqrt[n]{P_1 * P_2 * P_3 * \ldots * P_n}, \tag{2}$$

where n refers to a number of the coil images.

It should be noted that process 500 described above is provided for the purposes of illustration, and not intended to limit the scope of the present disclosure. Apparently for persons having ordinary skills in the art, numerous variations and modifications may be conducted under the teaching of the present disclosure. However, those variations and modifications do not depart the protecting scope of the present disclosure. In some embodiments, in 510, multiple pixel coordinates may be determined and the pixel values of these multiple pixels in reconstructed image may be determined at the same time. In some embodiments, in 510, a pixel coordinates may be determined. In that case, pixel values of pixels in reconstructed image may be determined successively. Similar modifications should fall within the scope of the present disclosure.

Figure 6:
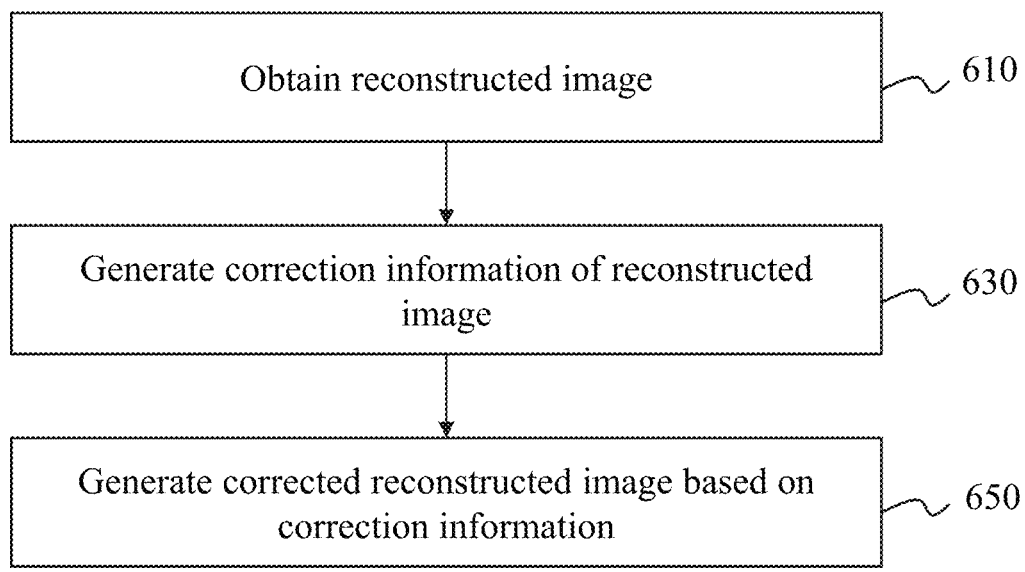
FIG. 6 is a flowchart illustrating an exemplary process for correcting a reconstructed image in accordance with some embodiments of the present disclosure.

FIG. 6 is a flowchart illustrating an exemplary process 600 for correcting a reconstructed image in accordance with some embodiments of the present disclosure. In some embodiments, process 600 may be performed by correction module 350 in imaging processing device 120. In some embodiments, process 600 described with reference to FIG. 6 may be an exemplary process for achieving 430 shown in FIG. 4.

In 610, a reconstructed image may be obtained. The obtainment of the reconstructed image may be performed by reconstructed image obtainment unit 351. The reconstructed image may be a 4D reconstructed image, a 3D reconstructed image, or a 2D reconstructed image. The reconstructed image may be obtained from reconstruction module 330 or retrieved from another source (e.g., a database 150, a storage, etc.). One or more reconstructed images may be obtained in 610. The obtained more than one reconstructed images may be generated based on the same MR image data or coils images. The obtained more than one reconstructed images may be generated using a same reconstruction technique or different reconstruction techniques. More descriptions about image reconstruction be found elsewhere in the present disclosure. See, for example, FIG. 1 and FIG. 4 and the descriptions thereof.

In some embodiments, a first reconstructed image and a second reconstructed image may be obtained in 610. Merely by way of example, the first reconstructed image may be generated using an SOS algorithm, and the second reconstructed image may be generated using a GA algorithm. Both of the first reconstructed image and the second reconstructed image may be generated based on MR image data obtained by the same MRI device 110 from the same scan. In some embodiments, the reconstructed image may be transformed by a transformation algorithm (e.g., a log transformation algorithm, a polar transformation algorithm, etc.).

In 630, correction information about the reconstructed image may be generated. The correction information may be an approximate correction information. The generation of the correction information may be performed by correction information generation unit 353. The correction information may include correction information related to intensity inhomogeneity, image distortion information, gradient nonlinearity information, motion artifact information, color information, or the like, or a combination thereof.

The correction information may be generated based on one or more reconstructed images obtained in 610. The correction information may be generated by comparing multiple reconstructed image. For example, the correction information may be generated by dividing the multiple reconstructed images, or by subtracting the multiple reconstructed images from one other, or the like, or a combination thereof. The correction information may be generated based on one reconstructed image. For example, the correction information may be generated by smoothing the reconstructed image to capture or emphasize information of interest contained in the reconstructed image. As another example, if the reconstructed image is obtained from reconstruction module 330 based on multiple coil images in 610, the correction information may be generated based on spatial sensitivity of the multiple RF receiver coils.

In some embodiments, the correction information may be correction information related to intensity inhomogeneity. The correction information related to intensity inhomogeneity may be generated based on one or more reconstructed images. In the case of generating correction information related to intensity inhomogeneity based on one reconstructed image, the correction information related to intensity inhomogeneity may be generated by smoothing the reconstructed image. Smoothing an image may tend to capture or emphasize information of interest in the image while leaving out noise in the image. Therefore, the smoothed reconstructed image may be used to correct intensity inhomogeneity of a reconstructed image.

The reconstructed image may be smoothed using a smoothing algorithm. The smooth algorithm may include a low-pass filter algorithm, an additive smoothing algorithm, a digital filter algorithm, an exponential smoothing algorithm, a Kalman filter, a Kernel smoother algorithm, a Kolmogorov-Zurbenko filter algorithm, a Laplacian smoothing algorithm, a Ramer-Douglas-Peucker algorithm, a Savitzky-Golay smoothing filter algorithm, or the like, or a combination thereof. In some embodiment, a reconstructed image may be smoothed by low-pass filter. The low pass filter may be a Gaussian filter, a Butterworth filter, a Chebyshev filter, or the like, or a combination thereof.

In the case of generating correction information related to intensity inhomogeneity based on multiple reconstructed images, the correction information related to intensity inhomogeneity may be generated by dividing the multiple reconstructed image. For example, the correction information related to intensity inhomogeneity may be generated by dividing a first reconstructed image by a second reconstructed image. The first reconstructed image and the second reconstructed image may be generated based on a same MR image data set or a same set of multiple coil images. The divided reconstructed image of the first reconstructed image and the second reconstructed may contain correction information related to intensity inhomogeneity used to correct intensity inhomogeneity of the first reconstructed image and/or second reconstructed image. More descriptions about obtaining correction information related to intensity inhomogeneity on two reconstructed images may be found elsewhere in the present disclosure. See, for example, FIG. 7 and FIG. 9 and the descriptions thereof.

In 650, a corrected reconstructed image may be generated based on the correction information. The operation 650 may be performed by correction information application unit 355. In some embodiments, the correction information may be correction information related to intensity inhomogeneity. In 650, intensity inhomogeneity of reconstructed image may be corrected to generate a corrected reconstructed image.

Merely by way of example, a smoothed reconstructed image or a divided reconstructed image that may be used to correct intensity inhomogeneity may be generated in 630. The corrected reconstructed image may be generated by dividing the reconstructed image by the smoothed reconstructed image or the divided reconstructed image. Dividing the reconstructed image by the smoothed reconstructed image means dividing the pixel values of all pixels in the reconstructed image by the pixel values of corresponding pixels in the smoothed reconstructed image. A corresponding pixel in the smoothed reconstructed image may be a pixel having the same coordinates as the pixel in reconstructed image. Dividing the reconstructed image by the divided reconstructed means dividing the pixel values of all pixels in the reconstructed image by the pixel values of corresponding pixels in the divided reconstructed image. A corresponding pixel in the divided reconstructed image may be a pixel having the same coordinates as the pixel in reconstructed image.

It should be noted that process 600 described above is provided for the purposes of illustration, and not intended to limit the scope of the present disclosure. Apparently for persons having ordinary skills in the art, numerous variations and modifications may be conducted under the teaching of the present disclosure. However, those variations and modifications do not depart the protecting scope of the present disclosure. For example, in 650, the corrected reconstructed image may be generated by multiplying the reconstructed image by the reciprocal of the smoothed reconstructed image. Multiplying the reconstructed image by the reciprocal of the smoothed reconstructed image means multiplying the pixel values of all pixels in the reconstructed image by the reciprocals of the pixel values of corresponding pixels in the smoothed reconstructed image. The corresponding pixel in the smoothed reconstructed image may be a pixel having the same coordinates with of the pixel in reconstructed image. Similar modifications should fall within the scope of the present disclosure.

Figure 7:
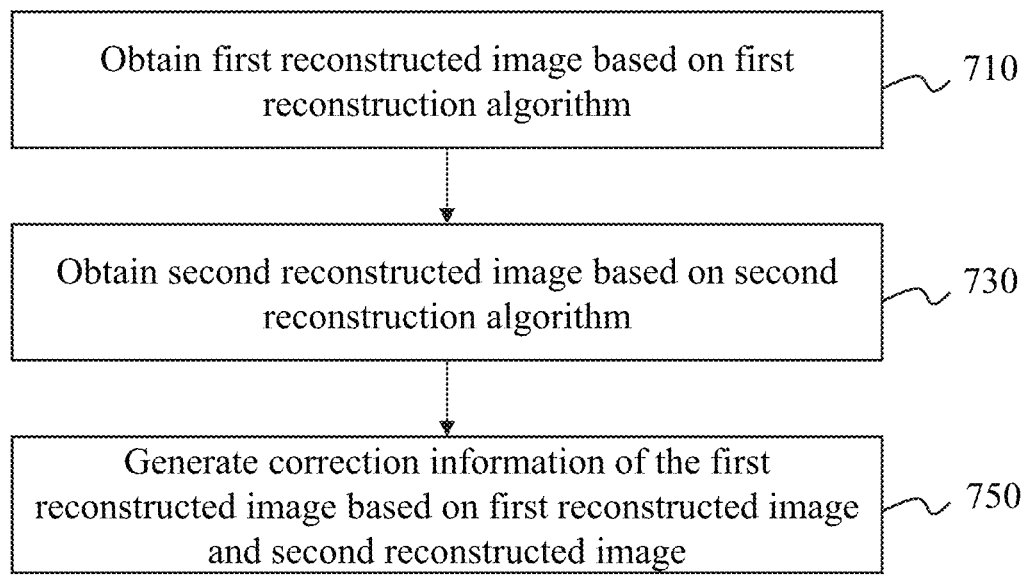
FIG. 7 is a flowchart illustrating an exemplary process for obtaining correction information in accordance with some embodiments of the present disclosure.

FIG. 7 is a flowchart illustrating an exemplary process 700 for obtaining correction information in accordance with some embodiments of the present disclosure. In some embodiments, process 700 may be performed by correction module 350 in imaging processing device 120. In some embodiments, process 700 described with reference to FIG. 7 may be an exemplary process for achieving 630 shown in FIG. 6.

In 710, a first reconstructed image based on a first reconstruction algorithm may be obtained. In 730, a second reconstructed image based on a second reconstruction algorithm may be obtained. The obtainment of the first reconstructed image and the second reconstructed image may be performed by reconstructed image obtainment unit 351. The reconstructed image may be a 3D MR reconstructed image or a 2D MR reconstructed image. The first reconstructed image and the second reconstructed image may be generated based on a same MR data set or a same set of coil images. The first reconstructed image and the second reconstructed image may be generated based on different reconstruction algorithms (e.g., an SOS algorithm, a GA algorithm, an iterative algorithm, etc.). More descriptions about image reconstruction may be found elsewhere in the present disclosure. See, for example, FIG. 1 and FIG. 4 and the descriptions thereof.

In some embodiments, the first reconstruction image may be generated based on an SOS algorithm and the second reconstruction image may be generated by a GA algorithm. More descriptions about the SOS algorithm and the GA algorithm may be found elsewhere in the present disclosure. See, for example, FIG. 5 and FIG. 9 and the descriptions thereof.

In 750, correction information of the first reconstructed image may be generated based on the first reconstructed image and the second reconstructed image. The correction information may include correction information related to intensity inhomogeneity, image distortion information, gradient nonlinearity information, motion artifact information, color information, or the like, or a combination thereof.

In some embodiments, the correction information may include correction information related to intensity inhomogeneity. The correction information related to intensity inhomogeneity may be generated based on the difference between the first reconstructed image and the second reconstructed image. Merely by way of example, the correction information related to intensity inhomogeneity may be determined by dividing the first reconstructed image by the second reconstructed image. Dividing the first reconstructed image by the second reconstructed image means dividing the pixel values of all pixels in the first reconstructed image by the pixel values of corresponding pixels in the second reconstructed image. A corresponding pixel in the second reconstructed image may be a pixel having the same coordinates as the pixel in the first reconstructed image. As another example, the correction information related to intensity inhomogeneity may be determined by dividing the second reconstructed image by the first reconstructed image.

Because the first reconstructed image and the second reconstructed image may be generated based on a same MR data set or a same set of coil images, they may contain the same structure information about an imaged object. Dividing the first reconstructed image by the second reconstructed image may provide the correction information of the first reconstructed image (e.g., the intensity inhomogeneity of the first reconstructed image.). More descriptions about generating correction information may be found elsewhere in the present disclosure. See, for example, FIG. 8 and the description thereof.

It should be noted that process 700 described above is provided for the purposes of illustration, and not intended to limit the scope of the present disclosure. Apparently for persons having ordinary skills in the art, numerous variations and modifications may be conducted under the teaching of the present disclosure. However, those variations and modifications do not depart the protecting scope of the present disclosure. For example, 710 and 730 may be performed at the same time. As another example, 730 may be performed before 710. Similar modifications should fall within the scope of the present disclosure.

Figure 8:
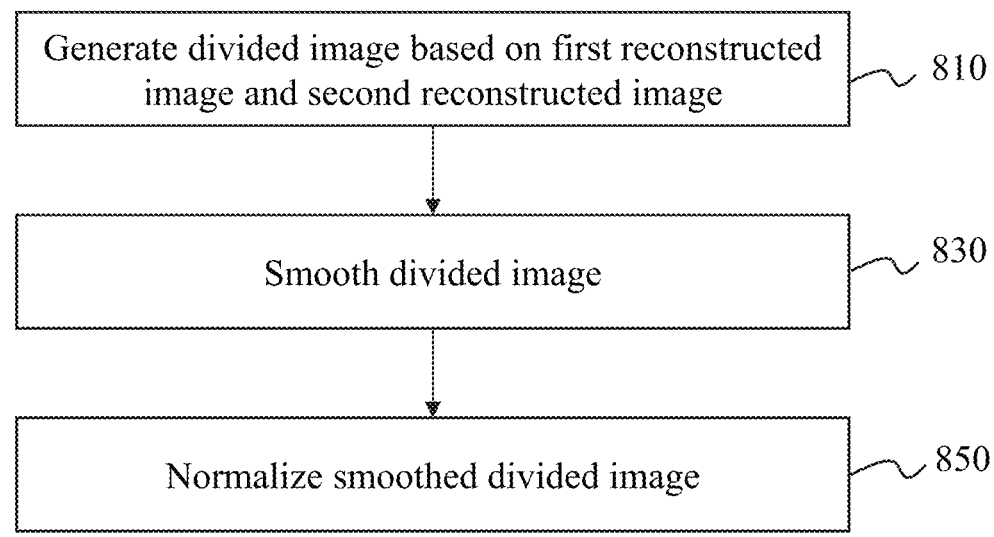
FIG. 8 is a flowchart illustrating an exemplary process for generating correction information in accordance with some embodiments of the present disclosure.

FIG. 8 is a flowchart illustrating an exemplary process 800 for generating correction information in accordance with some embodiments of the present disclosure. In some embodiments, process 800 may be performed by correction module 350 in imaging processing device 120. In some embodiments, process 800 described with reference to FIG. 8 may be an exemplary process for achieving 750 shown in FIG. 7.

In 810, a divided image may be generated based on a first reconstructed image and a second reconstructed image. A divided image may be generated by dividing the first reconstructed image by the second reconstructed image. The first reconstructed image and the second reconstructed image may be generated based on a same MR data set or a same coil images set. Dividing the first reconstructed image by the second reconstructed image means dividing the pixel values of all pixels in the first reconstructed image by the pixel values of corresponding pixels in the second reconstructed image. A corresponding pixel in the second reconstructed image may be a pixel having the same coordinates as the pixel in the first reconstructed image. More descriptions about divided image may be found elsewhere in the present disclosure. See, for example, FIG. 7 and the descriptions thereof.

In some embodiments, the first reconstructed image may be a reconstructed image generated based on an SOS algorithm and the second reconstructed image may be reconstructed generated based on a GA algorithm. The first reconstructed image and the second reconstructed may be generated based on a same MR data set or a same coil images set. In 810, the divided image may be generated by dividing the first reconstructed image based on the SOS algorithm by the second reconstructed image based on the GA algorithm.

In 830, the divided image may be smoothed to generate a smoothed divided image. Smoothing an image may tend to capture or emphasize information of interest in the image while leaving out noise, other fine-scale structure, or transient phenomena in the image. The divided image may be smoothed using a smoothing algorithm. In some embodiments, the divided image may be smoothed using a low-pass filter algorithm (e.g., a Gaussian filter, a Butterworth filter, a Chebyshev filter, etc.). More descriptions about smoothing image may be found elsewhere in the present disclosure. See, for example, FIG. 6 and the description thereof.

In 850, the smoothed divided image may be normalized. The operation of normalization may be used to make a correction reconstructed image and a reconstructed image have a same dynamic range. For example, the overall pixel values of the correction reconstructed image and the reconstructed image may be the same. As another example, the smoothed divided image may be normalized by adjusting the overall pixel values so that its average pixel value may equal to 1.

It should be noted that process 800 described above is provided for the purposes of illustration, and not intended to limit the scope of the present disclosure. Apparently for persons having ordinary skills in the art, numerous variations and modifications may be conducted under the teaching of the present disclosure. However, those variations and modifications do not depart the protecting scope of the present disclosure. For example, 830 may be omitted. As another example, 850 may be omitted. As another example, 810 may be performed by multiplying the first reconstructed image by the count backwards of the second reconstructed image. As another example, 850 may be performed before 830. The divided image may be normalized first and be smoothed then. Similar modifications should fall within the scope of the present disclosure.

Figure 9:
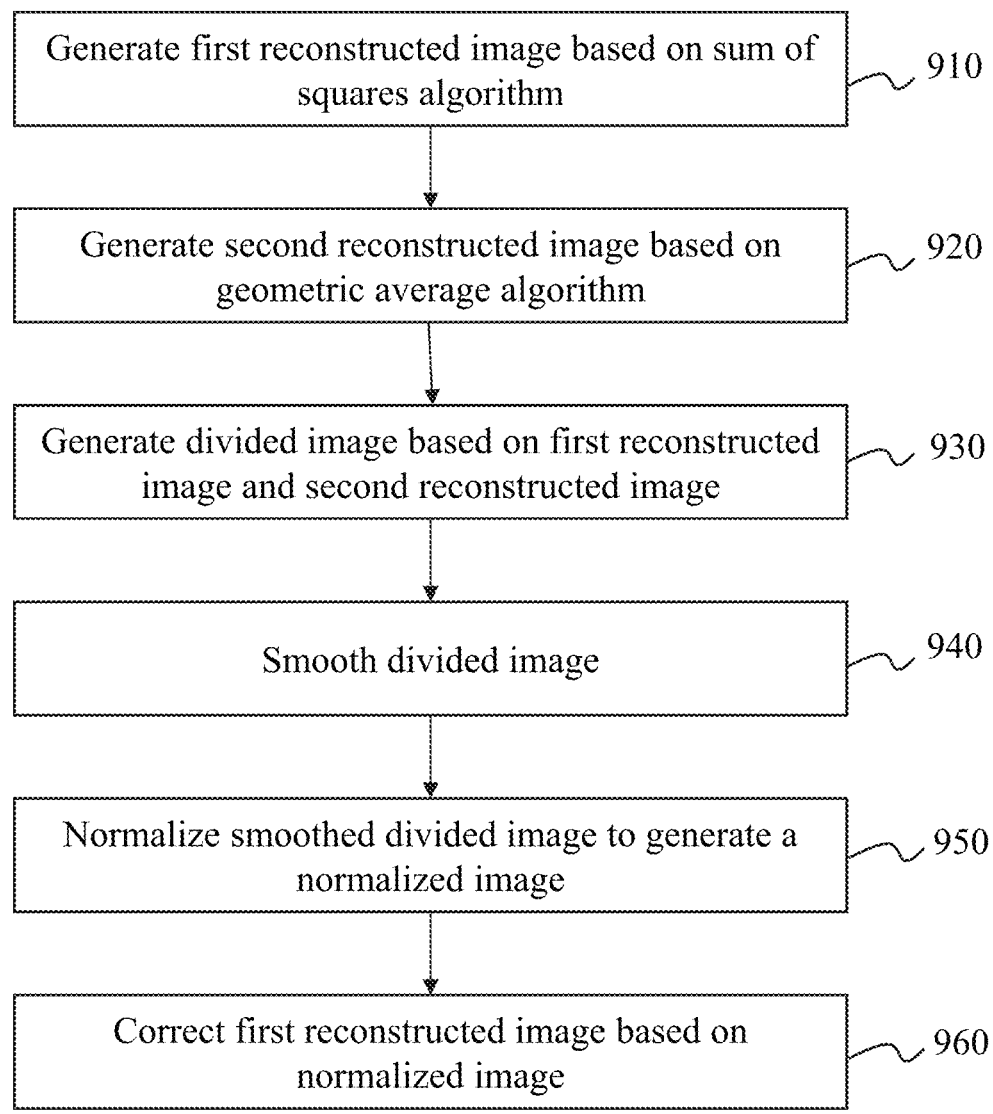
FIG. 9 is a flowchart illustrating an exemplary process for image reconstruction in accordance with some embodiments of the present disclosure.

FIG. 9 is a flowchart illustrating an exemplary process 900 for image reconstruction in accordance with some embodiments of the present disclosure. In some embodiments, process 900 may be performed by one or more devices (e.g., image processing device 120) in imaging system 100 (shown in FIG. 1) and image processing device 120 (shown in FIG. 3A). In some embodiments, at least part of process 900 may be performed by computer 200 shown in FIG. 2. In some embodiments, process 900 described with reference to FIG. 9 may be an exemplary embodiment of process 400 shown in FIG. 4.

In 910, a first reconstructed image based on an SOS algorithm may be generated. In 920, a second reconstructed image based on a GA algorithm may be generated. The first reconstructed image and/or the second reconstructed image may be a 3D MR reconstructed image or a 2D MR reconstructed image. The first reconstructed image and the second reconstructed image may be generated based on a same set of coil images by reconstruction module 330 of image processing device 120. Merely by way of example, the first reconstructed image may be generated by an SOS reconstruction unit 331 and the second reconstructed image may be generated by a GA reconstruction unit 333. More descriptions about the SOS algorithm and the GA algorithm may be found elsewhere in the present disclosure. See, for example, FIG. 5 and the descriptions thereof.

The first reconstructed image and the second reconstructed image may have intensity inhomogeneity due to the spatial sensitivity of coils. The SOS algorithm may be sensitive to spatial sensitivity of coils but not to noise. The GA algorithm may be sensitive to noise but not to spatial sensitive of the coils. Therefore, the first reconstructed image may tend to have a higher signal-to-noise ratio than the second reconstructed image. The first reconstructed image may tend to have higher intensity inhomogeneity than the second reconstructed image. The second reconstructed image may be used to correct the first reconstructed image.

Figure 10:
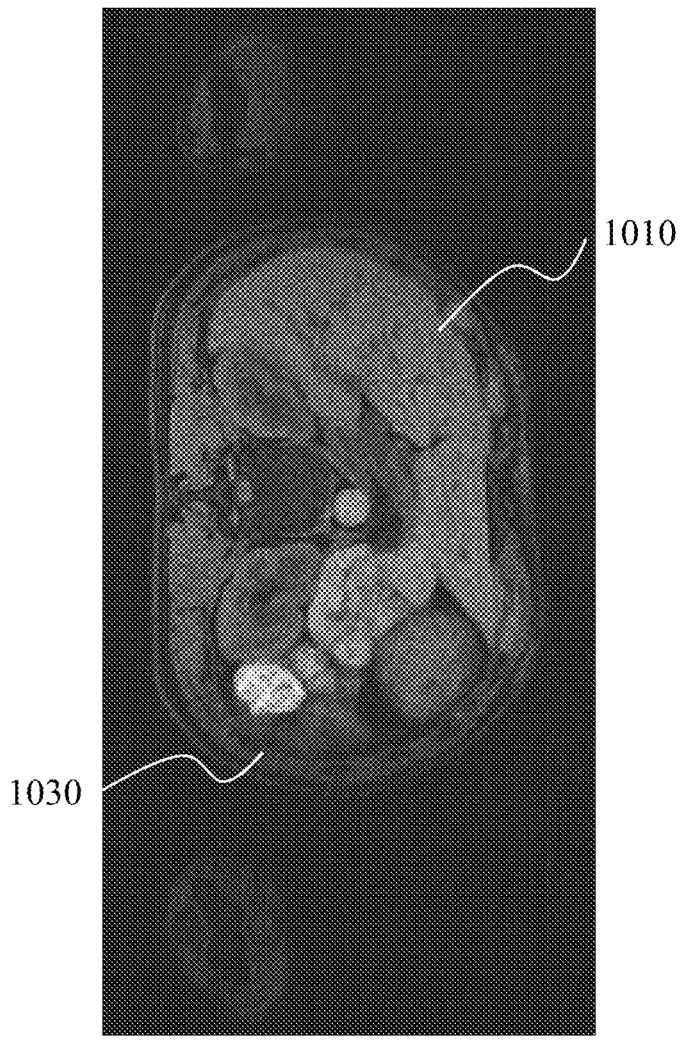
FIG. 10 illustrates a reconstructed liver image based on a GA algorithm.
Figure 11:
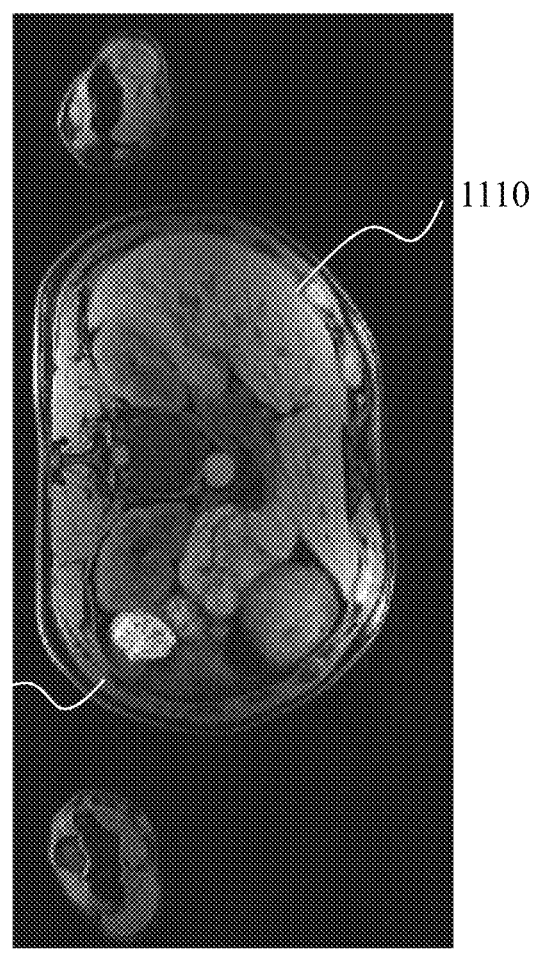
FIG. 11 illustrates a reconstructed liver image based on an SOS algorithm.

FIG. 10 illustrates a reconstructed image based on a GA algorithm. FIG. 11 illustrates a reconstructed image based on an SOS algorithm. As illustrated in FIG. 10 and FIG. 11, there are intensity inhomogeneity in the two reconstructed image. The intensity inhomogeneity in FIG. 11 is higher than that in FIG. 10.

In 930, a divided image may be generated based on the first reconstructed image and the second reconstructed image. The divided image may be generated by dividing the first reconstructed image by the second reconstructed image. Dividing the first reconstructed image by the second reconstructed image means dividing the pixel values of all pixels in the first reconstructed image by the pixel values of corresponding pixels in the second reconstructed image. A corresponding pixel in the second reconstructed image may be a pixel having the same coordinates with of the pixel in the first reconstructed image. The divided image may be used for correcting the first reconstructed image. More descriptions about divided image may be found elsewhere in the present disclosure. See, for example, FIG. 8 and the description thereof.

In 940, the divided image may be smoothed to generate a smoothed divided image. The divided image may be smoothed to remove or reduce noise while other information (e.g., correction information related to intensity inhomogeneity, etc.) may remain essentially. In some embodiments, the divided image may be smoothed using a low-pass filter algorithm (e.g., a Gaussian filter, a Butterworth filter, a Chebyshev filter, etc.). More descriptions about smoothing image may be found elsewhere in the present disclosure. See, for example, FIG. 6 and the descriptions thereof.

In 950, the smoothed divided image may be normalized to generate a normalized image. The operation of normalization may be used to make a correction reconstructed image and a reconstructed image (e.g., a reconstructed image based on an SOS algorithm) have a same dynamic range. For example, the overall pixel values of the correction reconstructed image and the reconstructed image may be the same. For another example, the smoothed divided image may be normalized by adjusting the overall pixel values so that its average pixel value may equal to 1.

In 960, the first reconstructed image may be corrected based on the normalized image. For example, the first reconstructed image may be corrected by dividing the first reconstructed image by the normalized image. Because the normalized image may contain intensity inhomogeneity of the first reconstructed image, the intensity inhomogeneity of the first reconstructed image may be corrected by dividing the first reconstructed image by the normalized image. Dividing the first reconstructed image by the normalized image means dividing the pixel values of all pixels in the first reconstructed image by the pixel values of corresponding pixels in the normalized image. A corresponding pixel in the normalized image may be a pixel having the same coordinates with of the pixel in the first reconstructed image.

It should be noted that process 900 described above is provided for the purposes of illustration, and not intended to limit the scope of the present disclosure. Apparently for persons having ordinary skills in the art, numerous variations and modifications may be conducted under the teaching of the present disclosure. However, those variations and modifications do not depart the protecting scope of the present disclosure. In some embodiments, some steps may be reduced or added. For example, 940 or 950 may be omitted. As another example, 930 may be performed before 910 or 930 and 910 may be performed at the same time. In some embodiments, 960 may be performed by multiplying the first reconstructed image by the count backwards of the normalized image. Similar modifications should fall within the scope of the present disclosure.

EXAMPLES

The examples are provided for illustration purposes, and not intended to limit the scope of the present disclosure.

Example 1

FIG. 10 illustrates a reconstructed liver image based a GA algorithm. FIG. 11 illustrates a reconstructed liver image based on an SOS algorithm. FIG. 10 and FIG. 11 were generated utilizing the system and process according to some embodiments of the present disclosure. The magnetic field intensity of the main magnet was 1.5 T. The slice thickness was 3 millimeters. The flip angle was 10°. The frequency was fat saturation. The TE of RF pulses was 2.2 milliseconds and the TR of RF pulses was 4.9 milliseconds. Forty layers of scanning was performed. Eighty coil images were generated. The BW of the reconstructed image was 345 Hz/pixel. The FOV of the reconstructed image was 260 millimeters*260 millimeters. The resolution of reconstructed image was 256*256.

As illustrated in FIG. 10 and FIG. 11, there are intensity inhomogeneity in the two reconstructed images. For example, the brightness of area 1010 is different from the brightness of area 1030. As another example, the brightness of area 1110 is different from the brightness of area 1130. The intensity inhomogeneity in FIG. 11 is higher than that in FIG. 10. The difference in brightness between area 1010 and area 1030 of FIG. 10 is less significant than the difference in brightness between area 1110 and area 1130 of FIG. 11.

Example 2

Figure 12:
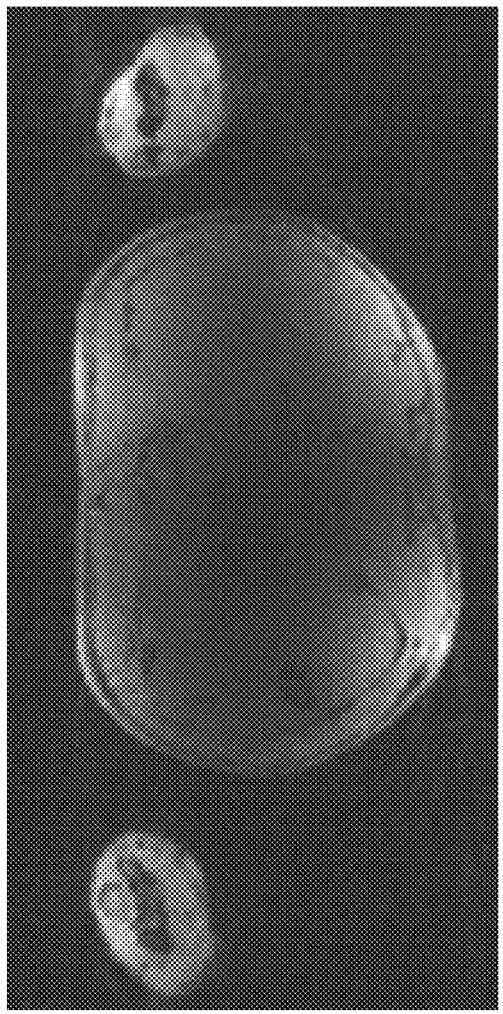
FIG. 12 illustrates a divided image of a reconstructed liver image based on an SOS algorithm and a reconstructed liver image based on a GA algorithm.

FIG. 12 illustrates a divided image of a reconstructed liver image based on an SOS algorithm (shown in FIG.11) and a reconstructed liver image based a GA algorithm (shown in FIG. 10.). The divided image in FIG. 12 was normalized. The divided image contains intensity inhomogeneity. The information related to intensity inhomogeneity of the divided image may be used to correct FIG. 11. As illustrated in FIG. 12, the intensity inhomogeneity changes smoothly and there is some noise in the divided image. FIG. 12 may be processed by a Gaussian filter to remove the noise in the divided image.

Example 3

Figure 13:
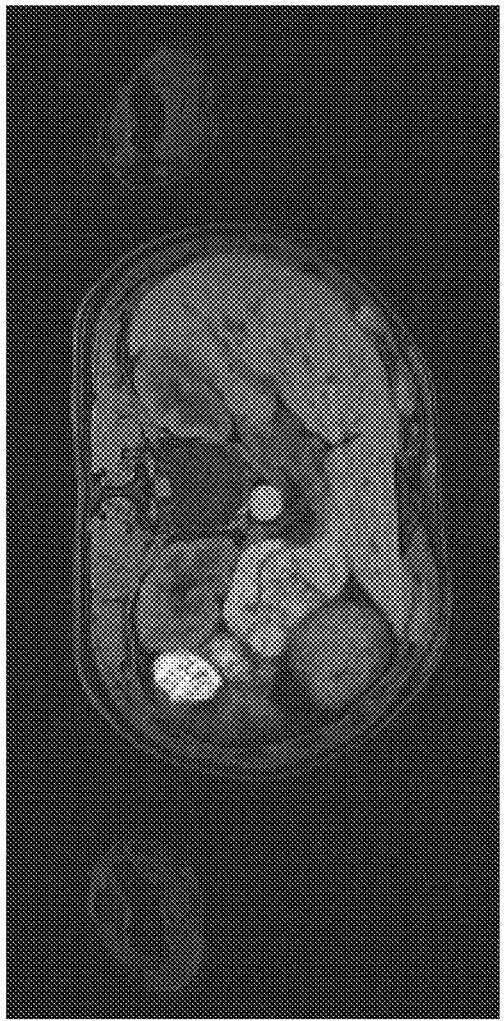
FIG. 13 illustrates a corrected image of a reconstructed liver image based on an SOS algorithm.

FIG. 13 illustrates a corrected image of a reconstructed liver image based on an SOS algorithm (shown in FIG. 11). FIG. 13 was generated by dividing FIG. 11 by the filtered image of FIG. 12. As illustrated in FIG. 13, the intensity inhomogeneity in FIG. 11 was corrected.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "block," "module," "engine," "unit," "component," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the operator's computer, partly on the operator's computer, as a stand-alone software package, partly on the operator's computer and partly on a remote computer or entirely on the remote computer or server. In the latter scenario, the remote computer may be connected to the operator's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution—e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities of ingredients, properties, and so forth, used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the descriptions, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

We claim:

1. A method for generating a corrected image implemented on a magnetic resonance imaging (MRI) system including an MRI device and a computing device, the MRI device including multiple radio frequency (RF) receiver coils, the computing device including a processor, the method comprising:
   receiving, by the multiple RF receiver coils, MR data of an object;
   reconstructing, by the processor, a first MR image based on the MR data according to a first reconstruction algorithm;
   reconstructing, by the processor, a second MR image based on the MR data according to a second reconstruction algorithm, the second reconstruction algorithm being different with the first reconstruction algorithm;
   generating, by the processor, correction information about the first MR image by dividing the first MR image by the second MR image; and
   generating, by the processor, the corrected image with reduced inhomogeneity intensity based on the first MR image and the correction information about the first MR image.

2. The method of claim 1, the first reconstruction algorithm or the second reconstruction algorithm including at least one of a sum of squares (SOS) algorithm, a geometric average (GA) algorithm, a sensitivity encoding (SENSE) algorithm, a parallel imaging with localized sensitivities (PILS) algorithm, a modified sensitivity encoding (MSENSE) algorithm, or a SPACE RIP algorithm.

3. The method of claim 1, the reconstructing an MR image based on the MR data including:
   generating multiple coil images based on the MR data, wherein each coil image is generated using a part of the MR data received by a corresponding RF receiver coil of the multiple RF receiver coils; and
   generating the MR image based on the multiple coil images.

4. The method of claim 3, wherein the reconstructing a first MR image or the reconstructing a second MR image further includes:
   for each point of a plurality of points in the imaged object, determining pixel coordinates of corresponding pixels in the multiple coil images relating to the point of the imaged object;
   obtaining pixel values of the corresponding pixels in the multiple coil images of the point; and
   reconstructing the first MR image or the second MR image based on the pixel coordinates and the pixel values of the corresponding pixels in the multiple coil images of the plurality of points in the imaged object.

5. The method of claim 1, wherein the correction information includes a divided image, and the generating the corrected image further includes:
   dividing the first MR image by the divided image.

6. The method of claim 1, wherein the correction information includes a divided image, and the generating correction information further includes:
   smoothing the divided image to generate a smoothed divided image; and
   normalizing the smoothed divided image to generate a normalized image.

7. The method of claim 6, wherein the generating the corrected image further includes:
   dividing the first MR image by the normalized image.

8. The method of claim 1, wherein the multiple RF receiver coils have different spatial sensitivities and receive MR signals in parallel.

9. A system comprising an MRI device and a computing device, the MRI device including multiple radio frequency (RF) receiver coils, the computing device including a processor, wherein during operation, the processor causes the system to:
receive, by the multiple RF receiver coils, MR data of an object;
reconstruct, by the processor, a first MR image based on the MR data according to a first reconstruction algorithm;
reconstruct, by the processor, a second MR image based on the MR data according to a second reconstruction algorithm, the second reconstruction algorithm being different with the first reconstruction algorithm;
generate, by the processor, correction information about the first MR image by dividing the first MR image by the second MR image; and
generate, by the processor, a corrected image with reduced inhomogeneity intensity based on the first MR image and the correction information about the first MR image.

10. The system of claim 9, the first reconstruction algorithm or the second reconstruction algorithm including at least one of a sum of squares (SOS) algorithm, a geometric average (GA) algorithm, a sensitivity encoding (SENSE) algorithm, a parallel imaging with localized sensitivities (PILS) algorithm, a modified sensitivity encoding (MSENSE) algorithm, or a SPACE RIP algorithm.

11. The system of claim 9, wherein to reconstruct an MR image, the processor further causes the system to:
generate multiple coil images based on the MR data, wherein each coil image is generated using a part of the MR data received by a corresponding RF receiver coil of the multiple RF receiver coils; and
generate the MR image based on the multiple coil images.

12. The system of claim 11, wherein to reconstruct the first MR image or the second MR image, the processor further causes the system to:
for each point of a plurality of points in the imaged object,
determine pixel coordinates of corresponding pixels in the multiple coil images relating to the point of the imaged object;
obtain pixel values of the corresponding pixels in the multiple coil images of the point; and
reconstruct the first MR image or the second MR image based on the pixel coordinates and the pixel values of the corresponding pixels in the multiple coil images of the plurality of points in the imaged object.

13. The system of claim 9, wherein the correction information includes a divided image, and to generate the corrected image, the processor further causes the system to:
divide the first MR image by the divided image.

14. The system of claim 9, wherein the correction information includes a divided image, and to generate the correction information, the processor further causes the system to:
smooth the divided image to generate a smoothed divided image; and
normalize the smoothed divided image to generate a normalized image.

15. The system of claim 14, wherein to generate the corrected image, the processor further causes the system to:
divide the first MR image by the normalized image.

16. The system of claim 9, wherein the multiple RF receiver coils have different spatial sensitivities and receive MR signals in parallel.

17. A non-transitory computer readable medium comprising executable instructions that, when executed by at least one processor, cause the at least one processor to effectuate a method comprising:
receiving MR data of an object, the MR data being acquired by multiple RF receiver coils of an MR device;
reconstructing, by the at least one processor, a first MR image based on the MR data according to a first reconstruction algorithm;
reconstructing, by the at least one processor, a second MR image based on the MR data according to a second reconstruction algorithm, the second reconstruction algorithm being different with the first reconstruction algorithm;
generating, by the at least one processor, correction information about the first MR image by dividing the first MR image by the second MR image; and
generating, by the at least one processor, a corrected image with reduced inhomogeneity intensity based on the first MR image and the correction information about the first MR image.

18. The non-transitory computer readable medium of claim 17, the first reconstruction algorithm or the second reconstruction algorithm including at least one of a sum of squares (SOS) algorithm, a geometric average (GA) algorithm, a sensitivity encoding (SENSE) algorithm, a parallel imaging with localized sensitivities (PILS) algorithm, a modified sensitivity encoding (MSENSE) algorithm, or a SPACE RIP algorithm.

19. The non-transitory computer readable medium of claim 17, the method further comprising:
generating multiple coil images based on the MR data, wherein each coil image is generated using a part of the MR data received by a corresponding RF receiver coil of the multiple RF receiver coils; and
generating the MR image based on the multiple coil images.

20. The non-transitory computer readable medium of claim 19, the method further comprising:
for each point of a plurality of points in the imaged object,
determining pixel coordinates of corresponding pixels in the multiple coil images relating to the point of the imaged object;
obtaining pixel values of the corresponding pixels in the multiple coil images of the point; and
reconstructing the first MR image or the second MR image based on the pixel coordinates and the pixel values of the corresponding pixels in the multiple coil images of the plurality of points in the imaged object.

* * * * *